United States Patent [19]

Berge et al.

[11] Patent Number: 4,861,789
[45] Date of Patent: Aug. 29, 1989

[54] DIHYDRO-INDENE-AMINE-DIHYDROOX-AZOLES

[75] Inventors: John Berge; Lee J. Beeley, both of Epsom, England

[73] Assignee: Beecham Group plc, Middlesex, England

[21] Appl. No.: 47,720

[22] Filed: May 4, 1987

[30] Foreign Application Priority Data

May 3, 1986 [GB] United Kingdom ............... 8610909

[51] Int. Cl.$^4$ ............... C07D 277/18; C07D 263/28; C07D 233/50; A61K 31/42
[52] U.S. Cl. ............................ 514/370; 514/377; 514/392; 548/190; 548/193; 548/234; 548/315
[58] Field of Search ............... 548/234, 315, 190, 193; 514/377, 370, 392

[56] References Cited

U.S. PATENT DOCUMENTS

| | | | |
|---|---|---|---|
| 2,870,159 | 1/1959 | Bloom | 548/234 |
| 2,870,161 | 1/1959 | Bloom | 548/234 |
| 2,883,410 | 4/1959 | Bloom | 260/456 |
| 3,432,600 | 3/1969 | Harvey | 424/272 |
| 3,679,798 | 7/1972 | Culik | 548/234 |
| 3,882,229 | 5/1975 | May et al. | 424/273 |
| 4,221,798 | 9/1980 | Cohnen | 548/234 |

FOREIGN PATENT DOCUMENTS 1195323 6/1965 Fed. Rep. of Germany .
1670751 1/1970 Fed. Rep. of Germany .
1670753 7/1970 Fed. Rep. of Germany .

OTHER PUBLICATIONS

Gas Online RNS 10169-43-7 & 102280-54-6.

*Primary Examiner*—Robert Gerstl
*Attorney, Agent, or Firm*—Hopgood, Calimafde, Kalil, Blaustein & Judlowe

[57] ABSTRACT

A compound of formula (I):

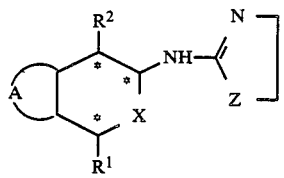

or a pharmaceutically acceptable acid addition salt and/or a pharmaceutically acceptable solvate thereof, wherein A represents a residue of a benzene ring optionally having up to four substituents selected from the group consisting of halogen, $C_{1-6}$ alkyl aNd $C_{1-6}$ alkoxy; $R^1$ and $R^2$ each independently represent a hydrogen atom or a $C_{1-6}$ alkyl group; X represents a bond or a moiety $CHR^1$ wherein $R^1$ is as defined above; and Z represents O, NH or S.

23 Claims, No Drawings

DIHYDRO-INDENE-AMINE-DIHYDROOX-AZOLES

The present invention relates to certain 2-substituted amino-4,5-dihydrooxazole, 2-substituted amino-4,5-dihydrothiazole and 2-substituted amino-4,5-dihydroimidazole derivatives, to a process for preparing such compounds, to pharmaceutical compositions containing such compounds and the use of such compounds and compositions in medicine.

U.S. Pat. No. 2,870,159 discloses certain 2-(1,2,3,4-tetrahydro-1-naphthylamino)-oxazolines, 2-(1,2,3,4,5,6,7,8-octahydro-1-naphthylamino)-oxazolines and 2-(1,2,3,4,5,6,7,8,9,10-decahydro-1-naphthylamino)-oxazolines. These compounds are disclosed as being central nervous system regulators.

U.S. Pat. No. 2,870,161 discloses certain substituted and unsubstituted 2-(1-indanylamino)-oxazolines. These compounds are disclosed as being useful regulators of the central nervous sytem.

U.S. Pat. No. 3,432,600 discloses certain 2-substituted oxazolines of formula (A):

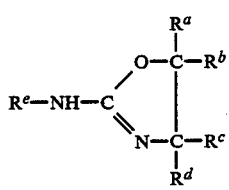

(A)

wherein $R^a$, $R^b$, $R^c$ and $R^d$ can each be hydrogen or an alkyl group of 1 through 4 carbons, with the total number of carbons in these substituents being a maximum of 8; and $R^e$ is:

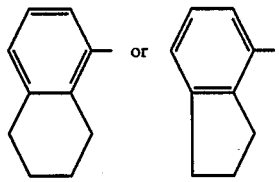

The compounds of formula (A) are disclosed as having anti-hypertensive and central nervous system depressant activity.

It has now surprisingly been discovered that a novel series of 2-substituted amino-4,5-dihydrooxazoles, 2-substituted amino-4,5-dihydrothiazoles and 2-substituted amino-4,5-dihydroimidazoles have useful $\alpha_2$-adrenergic properties and are therefore potentially useful in the treatment of conditions associated with an adrenergic imbalancer at the $\alpha_2$-receptor. They are therefore potentially useful in the treatment and/or prophylaxis of hyperglycaemia or hypoglycaemia. These compounds may also be useful in the treatment and/or prophylaxis of depression, glaucoma, hypertension or for inhibiting blood platelet aggregation.

Accordingly, the present invention provides a compound of formula (I):

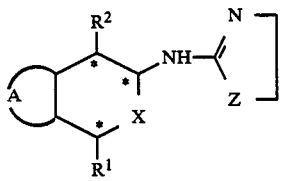

(I)

or a pharamaceutically acceptable acid addition salt and/or a pharamaceutically acceptable solvate thereof, wherein A represents a residue of a substituted or unsubstituted aryl group;

$R^1$ and $R^2$ each independently represent a hydrogen atom or a $C_{1-6}$ alkyl group;

X represents a bond or a moiety $CHR^1$ wherein $R^1$ is as defined above; and Z represents O, NH or S.

Suitably A represents a residue of an unsubstituted aryl group. Suitably, A represents a residue of a substituted aryl group.

Suitably, A represents a residue of a benzene ring optionally having up to 4, preferably up to 2 substituents.

Suitably, $R^1$ and $R^2$ represent hydrogen. Suitably at least one of $R^1$ and $R^2$ represents $C_{1-6}$ alkyl, the other represents hydrogen. Suitably, $R^1$ and $R^2$ represent $C_{1-6}$ alkyl.

Suitable substituents for any moiety A include halogen, $C_{1-6}$ alkyl, $C_{1-6}$ alkoxy, aryl, aryloxy or arylalkoxy.

In one suitable aspect the present invention provides a compound of formula (IA):

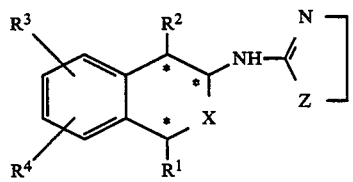

(IA)

or a pharmaceutically acceptable acid addition salt and/or a pharmaceutically acceptable solvate thereof, wherein $R^1$ and $R^2$ each independently represents a hydrogen atom or a $C_{1-6}$ alkyl group; $R^3$ and $R^4$ each independently represents a hydrogen or halogen atom, a $C_{1-6}$ alkyl or $C_{1-6}$ alkoxy group; X represents a bond or a moiety $CHR^1$ wherein $R^1$ is as defined above; and Z represents O, NH, or S.

Suitably, Z represents O. Suitably, Z represents NH. Suitably, Z represents S. Suitably, X represents a bond.

In a further preferred aspect the present invention provides a compound of formula (II):

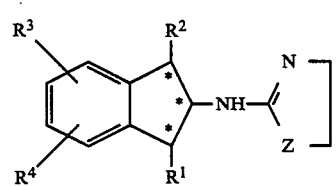

(II)

or a pharmaceutically acceptable acid addition salt thereof, wherein $R^1$, $R^2$, $R^3$, $R^4$ and Z are as defined in relation to formula (I).

Suitably, $R^3$ represents hydrogen, halogen or $C_{1-6}$ alkyl. Suitably, $R^3$ represents hydrogen. $R^3$ represents halogen. Suitably, $R^3$ represents $C_{1-6}$ alkyl.

Suitably, $R^4$ represents hydrogen. Preferably, $R^3$ represents hydrogen, chlorine or methyl. Preferably, $R^3$ represents hydrogen. Preferably, $R^3$ represents chlorine. Preferably, $R^3$ represents methyl.

The carbon atoms marked with an asterisk in formula (I) may be chiral carbon atoms depending upon the particular values of A, $R^1$ and $R^2$. Thus a compound of formula (I), or the pharmaceutically acceptable acid addition salts and/or solvates thereof, may exist in up to eight stereoisomers. All such isomers are encompassed by the present invention whether in the form of individual isomers or as mixtures of isomers.

The compounds of formula (I), or the pharmaceutically acceptable acid addition salts and/or solvates thereof, wherein A and Z are as defined above and X represents a bond and $R^1$ and/or $R^2$ represents $C_{1-6}$ alkyl may also exist as geometric isomers. All such isomers are encompassed by the present invention whether in the form of individual isomers or as mixtures of isomers.

Thus for example those compounds of formula (I) or the pharmaceutically acceptable salts and/or solvates thereof wherein X represents a bond, $R^1$ represents $C_{1-6}$ alkyl and $R^2$ represents hydrogen, may exist as cis- or trans-isomers depending upon the relative orientation of the

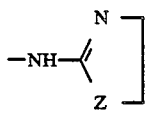

moiety and the $R^1$ group. about the carbon-carbon bond which separates them. It will be further appreciated that each geometric isomer will be present as an enantiomeric pair of stereoisomers.

All such isomers are encompassed by the present invention whether as single isomers or as mixtures of isomers.

Suitably, the abovementioned compounds of formula (I) wherein X represents a bond, $R^1$ represents $C_{1-6}$ alkyl and $R^2$ represents hydrogen are provided as the cis-isomer.

Suitably, the abovementioned compounds of formula (I) wherein X represents a bond, $R^1$ represents $C_{1-6}$ alkyl and $R^2$ represents hydrogen are provided as the trans-isomer.

It will be appreciated that the compounds of formula (IA), (II), (III) and (V) mentioned herein may also show analogous isomerisation to the compounds of formula (I).

The present invention also encompasses the pharmaceutically acceptable solvates of the compounds of formula (I), or the pharmaceutically acceptable salts thereof. A suitable solvate is the hydrate.

In a particular aspect the present invention provides a compound selected from the list consisting of:
2-[2-(2,3-dihydro-1H-indene)amino]-4,5-dihydrooxazole;
2-[2-(2,3-dihydro-1H-indene)amino]-4,5-dihydroimidazole;
2-[2-(4-chloro-2,3-dihydro-1H-indene)amino]-4,5-dihydrooxazole;
2-[2-(5-chloro-2,3-dihydro-1H-indene)amino]-4,5-dihydrooxazole;
2-[2-(2,3-dihydro-5-methyl-1H-indene)amino]-4,5-dihydrooxazole;
2-[cis-2-(2,3-dihydro-1-methyl-1H-indene)amino]-4,5-dihydrooxazole;
2-[trans-2-(2,3-dihydro-1-methyl-1H-indene)amino]-4,5-dihydrooxazole;
2-[2-(1,2,3,4-tetrahydronaphthyl)amino]4,5-dihydrooxazole; and
2-[2-(2,3-dihydro-1H-indene)amino]4,5-dihydrothiazole;

or a pharmaceutically acceptable acid addition salt and-/or a pharmaceutically acceptable solvate thereof.

When used herein the term "halogen" refers to fluorine, chlorine, bromine and iodine; preferably chlorine.

When used herein the term "$C_{1-6}$ alkyl" or the moiety "$C_{1-6}$ alk" as used for example in the moiety "$C_{1-6}$ alkoxy", relate to alkyl groups containing from 1 to 6 carbon atoms, which may be straight- or branched-chain e.g. a methyl, ethyl, n-propyl, isopropyl, n-butyl or tert-butyl group.

Suitable acid addition salts of the compound of formula (I) include pharmaceutically acceptable inorganic salts such as the sulphate, nitrate, phosphate, borate, hydrochloride and hydrobromide and pharmaceutically acceptable organic acid addition salts such as acetate, tartrate, maleate, citrate, succinate, benzoate, ascorbate, methane-sulphonate, α-keto glutarate, α-glycerophosphate, and glucose-1-phosphate.

Preferably the acid addition salt is a hemisuccinate, hydrochloride, α-ketoglutarate, or α-glycerophosphate in particular the hydrochloride salt.

In a further aspect the present invention provides a process for the preparation of a compound of formula (I), or a pharmaceutically acceptable acid addition salt and/or a pharmaceutically acceptable solvate thereof, which process comprises reacting a compound of formula (III):

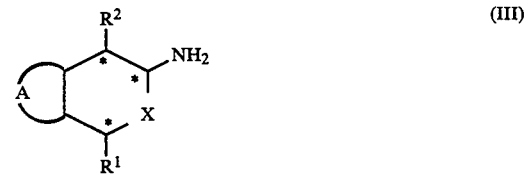

wherein $R^1$, $R^2$, A and X are as defined in relation to formula (I), with a compound of formula (IV) or a salt thereof:

wherein Z is as defined in relation to formula (I) and $R^5$ represents a $C_{1-6}$ alkyl group; and thereafter if required forming a pharmaceutically acceptable acid addition salt and/or a pharmaceutically acceptable solvate of the compound of formula (I).

Preferably, in the compound of formula (IV) Z represents NH.

A preferred salt of a compound (IV) is a hydrohalide and especially a hydroiodide.

The reaction between the compounds of formulae (III) and (IV) may be carried out in any suitable solvent, preferably an alcoholic solvent such as iso-amyl alcohol, suitably at an elevated temperature for example within the range of from 80° C. to 140° C. such as 120° to 130° C.

Suitably, $R^5$ represents a methyl or iso-propyl group.

The compounds of formulae (IV) are either known commercially available compounds or may be prepared by methods analogous to those used for the preparation of known compounds, for example those disclosed in the Journal of the American Chemical Society, 73, 602, 1951.

In a particular aspect the present invention further provides a process for the preparation of a compound of the hereinbefore defined formula (I), wherein Z represents O or S, which process comprises cyclising a compound of formula (V):

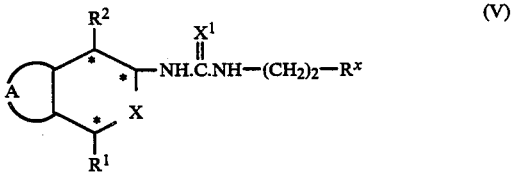

wherein $R^1$, $R^2$, A and X are as defined in relation to formula (I) and $R^x$ represents a leaving group; and thereafter if required forming a pharmaceutically acceptable acid addition salt of the compound of formula (I).

A suitable leaving group $R^x$ is a halogen atom, preferably a chlorine atom.

Suitably, the cyclisation is accomplished by heating the appropriate compound of formula (V), preferably in the presence of water for example by suspending the compound of formula (V) in water.

The compounds of formula (V) are novel compounds and as such form a further aspect of the present invention.

Accordingly, the present invention also provides a compound of the hereinbefore defined formula (V), useful as an intermediate in the preparation of a compound of the hereinbefore defined formula (I), wherein Z represents O or S.

The compounds of formula (V) may be prepared by reaction of a compound of the abovedefined formula (III) with a compound of formula (VI):

$$R^x-(CH_2)_2-NC=X^1 \quad (VI)$$

wherein $R^x$ is as defined in relation to formula (V) and $X^1$ represents O or S.

The reaction between the compounds of formulae (III) and (VI) may be carried out in any suitable inert solvent, suitably at a temperature of between 0° C. and 100° C., for example in toluene at 10° C. to 30° C.

The abovementioned isomers of the compounds of formula (I), and the pharmaceutically acceptable acid addition salts and/or solvates thereof, may be prepared by any conventional stereoselective synthesis.

Thus for example the compounds of formula (I) wherein X represents a bond, $R^1$ represents $C_{1-6}$ alkyl and $R^2$ represents hydrogen may be prepared as cis or trans isomers:

(i) by reaction of the appropriate cis or trans isomer of the compound of formula (III) with a compound of the formula (IV); or (ii) by cyclising the appropriate cis or trans isomer of the compound of formula (V);

and thereafter if required preparing a pharmaceutically acceptable acid addition salt and/or a pharmaceutically acceptable solvate thereof.

The appropriate cis or trans isomer of the compound of formula (V) may be prepared by reaction of the appropriate cis or trans isomer of the compound of formula (III) with a compound of the formula (VI).

The compounds of formula (III) including the cis and trans isomers thereof are known compounds or may be prepared using analogous methods to these used to prepare known compounds, for example those disclosed in the Journal of the Chemical Society (C), 920, 1970.

The compounds of formulae (VI) are either known commercially available compounds or they may be prepared by methods analogous to those used for the preparation of known compounds.

The compounds of formula (I) have useful pharmaceutical properties. Accordingly the present invention provides a compound of formula (I), or a pharmaceutically acceptable acid addition salt and/or a pharmaceutically acceptable solvate thereof, for use as an active therapeutic substance.

Suitably, the present invention provides a compound of formula (I), or a pharmaceutically acceptable acid addition salt and/or a pharmaceutically acceptable solvate thereof, for use in the treatment of conditions associated with an adrenergic imbalance at the $\alpha_2$-receptor in the human or non-human mammal such as hyperglycaemia, hypoglycaemia, depression, glaucoma, hypertension and blood platelet aggregation.

In particular the invention provides a compound of formula (I), or a pharmaceutically acceptable acid addition salt and/or a pharmaceutically acceptable solvate thereof, for use in the treatment of conditions associated with glucose imbalance in the human or non-human mammal, such as hyperglycaemia or hypoglycemia.

The determination of whether a compound of the present invention will be useful in the treatment of hyperglycaemia or hypoglycaemia may be carried out using conventional methods in the art, for example those disclosed in European Patent Specifications, Publication Nos. 002385 and 0139921.

The present invention particularly provides a suitable compound of formula (I), or a pharmaceutically acceptable addition salt and/or solvate thereof, for use in the treatment and/or prophylaxis of hyperglycaemia.

Most particularly the present invention provides a compound selected from the list consisting of:

2-[2-(2,3-dihydro-1H-indene)amino]-4,5-dihydrooxazole;

2-[2-(2,3-dihydro-1H-indene)amino]-4,5-dihydroimidazole;

2-[2-(4-chloro-2,3-dihydro-1H-indene)amino]-4,5-dihydrooxazole;

2-[2-(5-chloro-2,3-dihydro-1H-indene)amino]-4,5-dihydrooxazole;

2-[2-(2,3-dihydro-5-methyl-1H-indene)amino]-4,5-dihydrooxazole;

2[cis-2-(2,3-dihydro-1-methyl-1H-indene)amino]-4,5-dihydrooxazole;

2-[2-(1,2,3,4-tetrahydronaphthyl)amino]4,5-dihydrooxazole; and

2-[2-(2,3-dihydro-1H-indene)amino]-4,5-dihydrothiazole;

or a pharmaceutically acceptable acid addition salt and/or a pharmaceutically acceptable solvate thereof, for use in the treatment and/or prophylaxis of hyperglycaemia, depression, glaucoma, hypertension or blood platelet aggregation, especially hyperglycaemia.

A compound of the general formula (I), or a pharmaceutically acceptable acid addition salt and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of formula (I), or a pharmaceutically acceptable acid addition salt and/or a pharmaceutically acceptable solvate thereof, and a pharmaceutically acceptable carrier therefor.

As used in the term "pharmaceutically acceptable" embraces compounds, compositions and ingredients for both human and veterinary use: for example the term "pharmaceutically acceptable acid addition salt" embraces a veterinarily acceptable acid addition salt.

The composition may, if desired, be in the form of a pack accompanied by written or printed instructions for use.

Usually the pharmaceutical compositions of the present invention will be adapted for oral administration, although compositions for administration by other routes, such as by injection or percutaneous absorption and, especially for the treatment and/or prophylaxis of glaucoma, topical application are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate, sodium lauryl sulphate or sucrose.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

As indicated above in relation to the treatment and/or prophylaxis of glaucoma, a compound of formula (I), or a pharmaceutically acceptable acid addition salt and/or solvate thereof, may also be administered as a topical formulation in combination with conventional topical excipients. Such formulations will of course be suitably adapted for administration to the eye.

The topical formulations of the present invention may be presented as, for instance, eye ointments, creams or lotions or eye drops or other conventional formulations suitable for administration to the eye, and may contain appropriate conventional additives such as preservatives, solvents to assist the drug penetration and emollients in ointments and creams. The formulations may also contain compatible conventional carriers, such as eye ointment, cream or lotion bases and solvents suitable for administration to the eye. Such carriers may be present to from about 20% up to about 99.5% of the formulation.

Suitable eye ointments, creams or lotions; eye drops or other conventional formulations suitable for administration to the eye are conventional formulations well known in the art, for example, as described in standard text books of pharmaceutics and cosmetics, such as Harry's Cosmeticology published by Leonard Hill Books, Remington's Pharmaceutical Sciences, and the British and US Pharmacopoeias.

Suitably, the compound of formula (I) or a pharmaceutially acceptable acid addition salt and/or solvate thereof, will comprise from about 0.5 to 20% by weight of the topical formulation, favourably from about 1 to 10%, for example 2 to 5%.

The present invention further provides a method for the treatment and/or prophylaxis of conditions associated with adrenergic imbalance at the $\alpha_2$-receptor in the human or non-human mammal such as hyperglycaemia, hypoglycaemia, depression, glaucoma, hypertension and blood platelet aggregation, which method comprises administering an effective, non-toxic amount of a compound of formula (I), or a pharmaceutically acceptable acid addition salt and/or a pharmaceutically acceptable solvent thereof, to a human or non-human mammal in need thereof.

In particular the present invention provides a method for the treatment and/or prophylaxis of hyperglycaemia, glaucoma, in the human or non-human mammal, which method comprises the administration of an effective non-toxic amount of a compound of formula (I) or a pharmaceutically acceptable acid addition salt and/or a pharmaceutically acceptable solvate thereof.

In one most particular aspect the present invention provides a method for the treatment and/or prophylaxis of hyperglycaemia, depression, hypertension or blood platelet aggregation, especially hyperglycaemia, in the human or non human mammal which method comprises administering an effective, non-toxic amount of a compound selected from the list consisting of:

2-[2-(2,3-dihydro-1H-indene)amino]-4,5-dihydroxazole;

2-[2-(2,3-dihydro-1H-indene)amino]-4, 5-dihydroimidazole;

2-[2-(4-chloro-2,3-dihydro-1H-indene)amino]-4,5-dihydrooxazole;

2-[2-(5-chloro-2,3-dihydro-1H-indene)amino]-4,5-dihydrooxazole;

2-[2-(2,3-dihydro-5-methyl-1H-indene)amino]-4,5-dihydrooxazole;

2-[cis-2-(2,3-dihydro-1-methyl-1H-indene)amino]-4,5-dihydrooxazole;

2-[2-(1,2,3,4-tetrahydronaphthyl)amino]4,5-dihydrooxazole; and

2-[2-(2,3-dihydro-1H-indene)amino]-4,5-dihydrothiazole;

or a pharmaceutically acceptable acid addition salt and/or a pharmaceutically acceptable solvate thereof, to a human or non-human mammal in need thereof.

Conveniently, the active ingredient may be administered as a pharmaceutical composition hereinbefore defined, and this forms a particular aspect of the present invention.

In treating conditions associated with adrenergic imbalance at the $\alpha_2$-receptor in humans the compound of the general formula, (I) or pharmaceutically acceptable acid addition salt and/or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 1500 mg. Thus for example in the treatment and/or prophylaxis of conditions associated with a glucose imbalance such as hyperglycaemia in humans, the active compound may be taken in doses, such as those described above, one to six times a day in a manner such that the total daily dose for a 70 kg adult will generally be in the range of from 0.1 to 6000 mg, and more usually about 1 to 1500 mg. Similarly for the treatment and/or prophylaxis of depression, glaucoma (via non-topical regimens), hypoglycaemia, hypertension or platelet aggregation in humans.

Similarly in treating conditions associated with adrenergic imbalance at the $\alpha_2$-receptor and in particular those conditions associated with glucose imbalance, especially hyperglycaemia, in non-human mammals, especially dogs, the active compound may be administered by mouth, usually once or twice a day and in an amount in the range of from about 0.025 mg/kg to 25 mg/kg, for example 0.1 mg/kg to 20 mg/kg.

A further aspect of the present invention is to provide the use of a compound of formula (I), or a pharmaceutically acceptable acid addition salt and/or a pharmaceutically acceptable solvate thereof, for the manufacture of a medicament for the treatment of conditions associated with adrenergic imbalance at the $\alpha_2$-receptor and in particular those conditions associated with glucose imbalance, especially hyperglycaemia.

No toxicological effects are indicated when a compound of formula (I), or a pharmaceutically acceptable acid addition salt thereof, is administered in any of the abovementioned dosage ranges.

The following Examples illustrate the invention but do not limit it in any way.

EXAMPLE 1

2-[2-(2,3-Dihydro-1H-indene)amino]4,5-dihydrooxazole

A suspension of 5.0 g (0.02 mole) of N-(2-chloroethyl)-N'-[2-(2,3-dihydro-1H-indene] urea in 50 ml of water was heated until all the solid had dissolved. The resultant solution was cooled and washed once with dichloromethane, neutralised with saturated sodium bicarbonate solution and extracted with dichloromethane. The organic phase was dried and evaporated to give the crude product. Recrystallisation from ethyl acetate afforded the title compound as a white solid, m.p. 128°–130°.

$^1$H nmr $\delta$ (CDCl$_3$)

7.3–7.0 (4H, m); 4.9–4.4 (1H, broad s, exchanges with D$_2$O); 4.4 (1H, m); 4.2 (2H, t, J=8.5); 3.75 (2H, t, J=8.5); 3.29 (2H, dxm, J=15.9); 2.83 (2H, dxm, J=15.9).

EXAMPLE 2

2-[2-(2,3-Dihydro-1H-indene)amino)4,5-dihydroimidazole hydrochloride hemihydrate A mixture of 0.865 g (0.0065 mole) of 2-amino-2,3-dihydro-1H-indene and 1.58 g (0.0065 mole) of 2-thiomethyl-4,5-dihydroimidazole hydroiodide in 5 ml of 3-methyl-1-butanol was heated under reflux for 12 h under nitrogen. The solution was cooled and evaporated to dryness. Ion exchange chromatography over IRA 400 (OH) eluting with ethanol-water 1:2 gave 2-[2-(2,3-dihydro-1H-indene)amino)4,5-dihydroimidazole as a white solid. This solid was dissolved in ethanol and treated with saturated ethereal hydrogen chloride the title compound, m.p. 210°–212°, crystallised on cooling.

$^1$H nmr $\delta$ (DMSO)

9.0 (1H, d, exchanges with D$_2$O); 8.7–8.0 (1H, broad m, exchanges with D$_2$O); 7.3–7.0 (4H, m); 4.42 (1H, m); 3.61 (4H, s); 3.31 (2H, dxm, J=15); 2.88 (2H, dxm, J=15).

EXAMPLE 3

2-[2-(4-Chloro-2,3-dihydro-1H-indene)amino]4,5-dihydrooxazole

A solution of 1.6 g (0.01 mole) of 2-amino-4-chloro-2,3-dihydro-1H-indene in 40 ml of dry toluene was treated dropwise with a solution of 0.85 ml (0.01 mole) of 2-chloroethylisocyanate in 10 ml of dry toluene. After stirring at room temperature for 3 h the urea was filtered off from the reaction mixture. This solid in 40 ml of water was heated until all the solid had dissolved. The resultant solution was cooled and washed once with diethyl ether neutralised with saturated sodium carbonate solution and extracted with dichloromethane. The extract was dried and evaporated to give the crude product. Recrystallisation from ethyl acetate gave the title compound as a white solid, m.p. 128°–129°.

$^1$H nmr $\delta$ (DMSO)

7.2 (3H, m); 6.67 (1H, broad s, exchanges with D$_2$O); 4.25 (1H, m); 4.15 (2H, t); 3.6 (2H, t); 3.2 (2H, m); 2.9 (2H, m).

EXAMPLE 4

2-[2-(5-Chloro-2,3-dihydro-1H-indene)amino]4,5-dihydrooxazole

The title compound, m.p. 132°–133° (ethyl acetate), was prepared from 2-amino-5-chloro-2,3-dihydro-1H-indene in an analogous method to that described in Example 3, $^1$H nmr $\delta$ (CDCl$_3$)

7.2 (3H, m); 4.56 (1H, broad s, exchanges with D$_2$O); 4.38 (1H, m); 4.25 (2H, t); 3.72 (2H, t); 3.28 (2H, m); 2.8 (2H, m).

EXAMPLE 5

2-[2-(2,3-dihydro-5-methyl-1H-indene)amino]4,5-dihydrooxazole

The title compound, m.p. 156°–157° (ethyl acetate), was prepared from 2-amino-2,3-dihydro-5-methyl-1H-indene in an analogous method to that described in Example 3.

$^1$H nmr $\delta$ (CDCl$_3$)

7.0 (3H, m); 4.4 (1H, m); 4.2 (2H, t); 3.73 (2H, t); 3.25 (2H, dd); 2.78 (2H, dd); 2.3 (3H, s).

EXAMPLE 6

2-[cis-2-(2,3-dihydro-1-methyl-1H-indene)amino]4,5-dihydrooxazole

The title compound, m.p. 92°–93° (ethyl acetate-petroleum ether 60°–80°), was prepared from cis-2-amino-2,3-dihydro-1-methyl-1H-indene in an analogous method to that described in Example 3.

$^1$H nmr $\delta$ (CDCl$_3$)

7.2 (4H, m); 4.45 (1H, m); 4.2 (2H, t); 3.75 (2H, t); 3.4 (1H, m); 3.2 (1H, dd); 2.85 (1H, dd); 1.22 (3H, d).

EXAMPLE 7

2-[Trans-2-(2,3-dihydro-1-methyl-1H-indene)amino]4,5-dihydrooxazole

The title compound, m.p. 78°–80° (ethyl acetate-petroleum ether 60°–80°), was prepared from trans-2-amino-2,3-dihydro-1-methyl-1H-indene in an analogous method to that described in Example 3.

$^1$H nmr $\delta$ (CDCl$_3$)

7.2 (4H, m); 4.27 (2H, t); 3.97 (1H, m); 3.8 (2H, t); 3.38 (1H, dd); 3.03 (1H, m); 2.75 (1H, dd); 1.35 (3H, d)

EXAMPLE 8

2-[2-(1,2,3,4-Tetrahydronaphthyl)amino]4,5-dihydrooxazole

The title compound, m.p. 131–132 (ethyl acetate), was prepared from 2-amino-1,2,3,4-tetrahydronaphthalene in an analogous method to that described in Example 3.

$^1$H nmr δ (CDCl$_3$)

7.1 (4H, m); 4.25 (2H, t); 3.95 (1H, m); 3.77 (2H, t); 3.17 (1H, dd); 2.87 (2H, t); 2.67 (1H, dd); 2.13 (1H, m); 1.78 (1H, m).

EXAMPLE 9

2-[2-(2,3-Dihydro-1H-indene)amino]4,5-dihydrothiazole

A solution of 3.1 g (0.023 mole) of 2-amino-2,3-dihydro-1H-indene in 50 ml of dry toluene was treated dropwise with a solution of 2.8 g (0.023 mole) of 2-chlorethylisothiocyanate in 10 ml of dry toluene. After stirring at room temperature for 3 h the thiourea was filtered off from the reaction mixture. This solid in 40 ml of water was heated until all the solid had dissolved. The resultant solution was cooled and washed once with diethyl ether, neutralised with saturated sodium carbonate solution and extracted with dichloromethane. The extract was dried and evaporated to give the crude product. Recrystallisation from ethyl acetate gave the title compound as a white solid, m.p. 162°–163°.

$^1$H nmr δ (CDCl$_3$) 7.18 (4H, m); 4.73 (1H, broad s, exchanges with D$_2$O); 4.5 (1H, m); 3.98 (2H, t); 3.73 (2H, t); 3.3 (2H, dd); 2.85 (2H, dd).

EXAMPLE X 1

N-(2-Chloroethyl)-N'-[2-(2,3-dihydro-1H-indene)]urea

A solution of 8.0 g (0.06 mole) of 2-amino-2,3-dihydro-1H-indene in 75 ml of dry toluene was treated dropwise with a solution of 5.1 ml (0.06 mole) of 2-chloroethyl isocyanate in 25 ml of dry toluene. After stirring at room temperature for 16 h the product was filtered off from the reaction mixture, washed once with 25 ml of toluene and dried under vacuum at 25°.

$^1$H-nmr δ (CDCl$_3$/DMSO)

7.3–7.0 (4H, m); 6.0–5.6 (2H, broad m, slow exchange with D$_2$O); 4.7–4.3 (1H, m); 3.7–3.3 (4H, m); 3.22 (2H, dxm, J=16); 2.75 (2H, dxm, J=16).

DEMONSTRATION OF EFFECTIVENESS OF COMPOUNDS

Reversal of Adrenaline-Exacerbated Glucose Intolerance in Mice

CFLP female mice of about 25 g were fasted for 24 hours prior to receiving water (10 ml/kg) or the compound by oral gavage. Thirty minutes later, glucose (1 g/kg) and adrenaline (300 μg/kg) were injected subcutaneously. Blood samples for glucose analysis were taken serially from the tail of each mouse at 0, 30, 60, 90 and 120 minutes after dosing glucose and the results are expressed below as the percentage reduction in the area under the blood glucose curve; the compound treated groups being compared to the water dosed control group. Six mice were used in each treatment group.

| Example | Dose (μmol/kg) | % Reduction in area under Blood Glucose Curve |
|---|---|---|
| 1 | 20 | 35 |
| 3 | 20 | 42 |
| 4 | 20 | 44 |
| 8 | 20 | 18 |
| 9 | 20 | 33 |

α2-Adrnoceptor Binding

Human platelet membranes were incubated with [$^3$H] Rauwolscine (0.5–1.0 nM) for 30 minutes at 30° C. with varying concetrates of the drug (0.1–10,000 nM). The binding assay was stopped by filtering and rinsing on GF B glass fibre filters.

Binding Affinity (Ki) was calculated using the Cheng-Prussoff equation.

| Example No: | Binding Affinity Ki (nM) |
|---|---|
| 1 | 1.0 |
| 2 | 98 |
| 3 | 1.0 |
| 4 | 25 |
| 5 | 25 |
| 6 | 2 |
| 7 | 2 |
| 9 | 190 |

We claim:

1. A compound of formula (I):

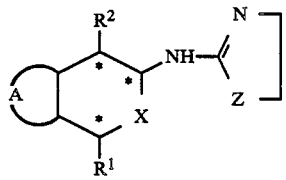

or a pharmaceutically acceptable acid addition salt and/or a pharmaceutically acceptable solvate thereof, wherein A represents a residue of a benzene ring optionally having up to four substituents selected from the group consisting of halogen, C$_{1-6}$ alkyl and C$_{1-6}$ alkoxy;

R$^1$ and R$^2$ each independently represent a hydrogen atom or a C$_{1-6}$ alkyl group;

X represents a bond or a moiety CHR$^1$ wherein R$^1$ is as defined above; and

Z represents O, NH or S.

2. A compound according to claim 1 of formula (IA):

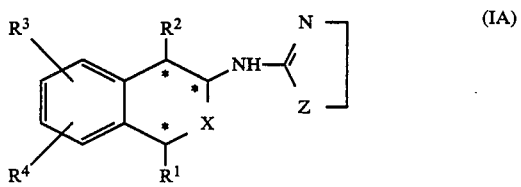

or a pharmaceutically acceptable acid addition salt and/or a pharmaceutically acceptable solvate thereof, wherein $R^1$ and $R^2$ each independently represents a hydrogen atom or a $C_{1-6}$ alkyl group;

$R^3$ and $R^4$ each independently represents a hydrogen or halogen atom, a $C_{1-6}$ alkyl or $C_{1-6}$ alkoxy group;

X represents a bond or a moiety $CHR^1$ wherein $R^1$ is as defined above; and

Z represents O, NH or S.

3. A compound according to claim 1, wherein Z represents O.

4. A compound according to claim 1 wherein Z represents NH.

5. A compound according to claim 1, wherein Z represents S.

6. A compound according to claim 1, wherein X represents a bond.

7. A compound according to claim 2, of formula (II):

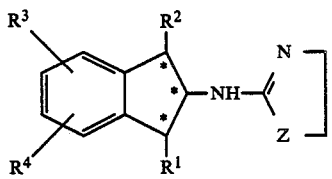

(II)

or a pharmaceutically acceptable acid addition salt or a pharmaceutically acceptable solvate thereof, wherein $R^1$, $R^2$, $R^3$, $R^4$ and Z are as defined in relation to formula (IA).

8. A compound according to claim 1, wherein $R^1$ represents hydrogen.

9. A compound according to claim 1, wherein $R^2$ represents hydrogen.

10. A compound according to claim 2, wherein $R^3$ represents hydrogen, halogen or $C_{1-6}$ L alkyl.

11. A compound according to claim 2, wherein $R^4$ represents hydrogen.

12. A compound according to claim 1, selected from the group consisting of:

2-[2-(2,3-dihydro-1H-indene)amino]-4,5-dihydrooxazole;

2-[2-(2,3-dihydro-1H-indene)amino]-4,5-dihydroimidazole;

2-[2-(4-chloro-2,3-dihydro-1H-indene)amino]-4,5-dihydrooxazle;

2-[2-(5-chloro-2,3-dihydro-1H-indene)amino]-4,5-dihydrooxazole;

2-[2-(2,3-dihydro-5-methyl-1H-indene)amino]-4,5-dihydrooxazole;

2-[cis-2-(2,3-dihydro-1-methyl-1H-indene)amino]-4,5-dihydrooxazole;

2-[trans-2-(2,3-dihyro-1-methyl-1H-indene)amino]-4,5-dihydrooxazole;

2-[2-(1,2,3,4-tetrahydronaphthyl)amino]4,5-dihydrooxazole; and

2-[2-(2,3-dihydro-1H-indene)amino]4,5-dihydrothiazole;

or a pharmaceutically acceptable acid addition salt and/or a pharmaceutically acceptable solvate thereof.

13. 2-[2-(2,3-Dihydro-1H-indene)amino]-4,5-dihydrooxazole; or a pharmaceutically acceptable acid addition salt and/or a pharmaceutically acceptable solvate thereof.

14. 2-[2-(2,3-Dihydro-1H-indene)amino]-4,5-dihydroimidazole; or a pharmaceutically acceptable acid addition salt and/or a pharmaceutically acceptable solvate thereof.

15. 2-[2-(4-Chloro-2,3-dihydro-1H-indene)amino]-4,5-dihydrooxazole; or a pharmaceutically acceptable acid addition salt and/or a pharmaceutically acceptable solvate thereof.

16. 2-[2-(5-Chloro-2,3-dihydro-1H-indene)amino]-4,5-dihydrooxazole; or a pharmaceutically acceptable acid addition salt and/or a pharmaceutically acceptable solvate thereof.

17. 2-[2-(2,3-Dihydro-5-methyl-1H-indene)amino]-4,5-dihydrooxazole; or a pharmaceutically acceptable acid addition salt and/or a pharmaceutically acceptable solvate thereof.

18. 2-[Cis-2-(2,3-dihydro-1-methyl-1H-indene)amino]-4,5-dihydrooxazole; or a pharmaceutically acceptable acid addition salt and/or a pharmaceutically acceptable solvate thereof.

19. 2-[Trans-2-(2,3-dihydro-1-methyl-1H-indene)amino]-4,5-dihydrooxazole; or a pharmaceutically acceptable acid addition salt and/or a pharmaceutically acceptable solvate thereof.

20. 2-[2-(2,3-Dihydro-1H-indene)amino]-4,5-dihydrothiazole; or a pharmaceutically acceptable acid addition salt and/or a pharmaceutically acceptable solvate thereof.

21. A pharmaceutical composition useful in the treatment of conditions associated with an adrenergic imbalance at the $\alpha_2$-receptor comprising a pharmaceutically acceptable amount of a compound of formula (I) according to claim 1, or a pharmaceutically acceptable acid addition salt and/or a pharmaceutically acceptable solvate thereof, and a pharmaceutically acceptable carrier therefor.

22. A method for the treatment and/or prophylaxis of conditions associated with adrenergic imbalance at the $\alpha^2$-receptor in the human or non-human mammal, which method comprises administering an effective, non-toxic amount of a compound of formula (I), according to claim 1 or a pharmaceutically acceptable acid addition salt and/or a pharmaceutically acceptable solvate thereof, to a human or non-human mammal in need thereof.

23. A method for the treatment and/or prophylaxis of hyperglycaemia in the human or non-human mammal which method comprises the administration of a suitable compound of formula (I) according to claim 1 or a pharmaceutically acceptable acid addition salt thereof and/or a pharmaceutically acceptable solvate thereof, to a human or non-human mammal in need thereof.

* * * * *

UNITED STATES PATENT AND TRADEMARK OFFICE
CERTIFICATE OF CORRECTION

PATENT NO. : 4,861,789

DATED : August 29, 1989

INVENTOR(S) : Lee James Beeley and John Berge

It is certified that error appears in the above-identified patent and that said Letters Patent is hereby corrected as shown below:

Column 1, line 60 - "imbalancer" should read "imbalance".

Column 6, line 43 - "002385" should read "0023385".

Column 7, line 15 - "in" should read "herein".

Column 7, line 63 - "present to" should read "present as".

IN THE CLAIMS

Claim 10, line 40, "L alkyl" in italics should read "alkyl" in normal print.

Signed and Sealed this

Twenty-fourth Day of September, 1991

Attest:

HARRY F. MANBECK, JR.

Attesting Officer

Commissioner of Patents and Trademarks